United States Patent
Moreno

(10) Patent No.: US 7,459,149 B2
(45) Date of Patent: Dec. 2, 2008

(54) TWO-PHASE COMPOSITION AND ITS USES IN COSMETICS

(75) Inventor: Angeles Fonolla Moreno, Paris (FR)

(73) Assignee: L'Oreal, Paris (FR)

( * ) Notice: Subject to any disclaimer, the term of this patent is extended or adjusted under 35 U.S.C. 154(b) by 140 days.

(21) Appl. No.: 11/302,170

(22) Filed: Dec. 14, 2005

(65) Prior Publication Data

US 2006/0153790 A1 Jul. 13, 2006

Related U.S. Application Data

(60) Provisional application No. 60/646,521, filed on Jan. 25, 2005.

(30) Foreign Application Priority Data

Jan. 3, 2005 (FR) .................................. 05 50009

(51) Int. Cl.
*A61K 7/06* (2006.01)

(52) U.S. Cl. ................. 424/70.12; 424/70.24; 510/130; 510/156; 510/417

(58) Field of Classification Search ................ 510/130, 510/156, 417; 424/70.12, 70.24
See application file for complete search history.

(56) References Cited

U.S. PATENT DOCUMENTS 5,955,408 A * 9/1999 Kaiser et al. ................. 510/131

2002/0010110 A1 * 1/2002 Hayward et al. ............ 510/130

FOREIGN PATENT DOCUMENTS

| DE | 3627313 | | 2/1988 |
|---|---|---|---|
| EP | 258558 | * | 3/1988 |
| WO | WO 99/13860 | * | 3/1999 |

* cited by examiner

*Primary Examiner*—Daniel Sullivan
*Assistant Examiner*—Chukwuma O Nwaonicha
(74) *Attorney, Agent, or Firm*—Oblon, Spivak, McClelland, Maier & Neustadt, P.C.

(57) ABSTRACT

A composition having two separate phases, one above the other, the composition containing:
(1) a bottom aqueous phase,
(2) a top oil-in-water emulsion, and
(3) at least one anionic surfactant chosen from the sodium salts of esters of dimethicone copolyol and sulphosuccinic acid.

The two-phase composition has good cosmetic qualities, it is very soft and fresh upon application, while having good efficacy. The invention also relates to the use of this composition in cosmetics, especially for removing makeup from, cleansing and/or caring for the skin, the lips and/or the eyes, or for hair care.

16 Claims, No Drawings

TWO-PHASE COMPOSITION AND ITS USES IN COSMETICS

REFERENCE TO PRIOR APPLICATIONS

This application claims priority to U.S. provisional application No. 60/646,521 filed Jan. 25, 2005, and to French patent application 0550009 filed Jan. 3, 2005, both incorporated herein by reference.

FIELD OF THE INVENTION

The present invention relates to a composition, preferably one intended for topical application, comprising two separate phases, an aqueous phase and an emulsion, these phases being readily mixed by shaking and readily undergoing phase separation after stopping the shaking. Another subject of the present invention is the use of this composition in cosmetics and dermatology, and especially for removing makeup from, cleansing and/or caring for the skin, the lips and/or the eyes, and/or for hair care.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Conventional makeup-removing compositions may be provided in various forms, for instance in the form of more or less fluid makeup-removing milks containing water, oils and surfactants, of foaming aqueous gels, or of oily compositions. Each of these galenic substances has advantages and disadvantages. Thus, the makeup-removing milks have the advantage of giving a pleasant sensation during application to the skin, of moisturizing the skin and of preserving the skin barrier, but they have the disadvantage of giving a more or less greasy feel, without freshness, and of leaving a film on the skin. The aqueous gels have the advantage of giving a good sensation of freshness, an immediate and persistent sensation of cleanness and a non-greasy feel, but they have the disadvantage of also giving a sensation of tightness (sticky quiet), and of being able to dry out the skin if use is too frequent. As for the makeup-removing oils, they have the advantage of moisturizing the skin, of preserving the skin barrier and of restoring the lipid balance of the skin, while being very effective for makeup removal, but they lack freshness, give a greasy feel and leave a greasy film on the skin.

To avoid the disadvantages of the prior art, compositions have been proposed which consist of two separate phases, especially an aqueous phase and an oily phase which are separate and not emulsified in each other at rest, which are generally referred to by the term "two-phase composition". They differ from emulsions by the fact that, at rest, the two phases are separate instead of being emulsified in each other. The use of these two-phase compositions requires prior shaking in order to extemporaneously form an emulsion, the latter needing to be of sufficient quality and stability to allow the uniform application of the two phases onto the skin or keratin material onto which it is applied. At rest, the phases must separate rapidly and regain their initial state, this phenomenon being known more commonly by the term "phase separation".

Two-phase compositions have already been described, for example in documents EP-A-370856 and EP-A-603080, especially for removing makeup from the eyes. These compositions have the advantage of being fresher upon application than the milks and the oily compositions, while being effective, and of not giving any sensation of tightness or irritation, while conferring softness on the skin. However, they have the disadvantage of not always giving a feeling of sufficient freshness and of not being easily removed.

The need therefore still remains for a two-phase composition which has excellent cosmetic qualities (softness, freshness, tolerance), and a very good efficacy both for makeup removal and for care.

SUMMARY OF THE INVENTION

Surprisingly, the inventor has found that the use of particular surfactants in a two-phase composition containing an emulsified (top) phase and an aqueous (bottom) phase makes it possible to obtain a two-phase composition having the desired qualities, i.e. very effective but also very soft and fresh upon application. These surfactants have the advantage of being very well tolerated, including for application to the eyes which are particularly sensitive to compounds which may be aggressive.

DETAILED DESCRIPTION OF THE INVENTION

One subject of the invention is a composition, preferably formulated for topical application, comprising two separate phases, one above the other when they are in direct contact, comprising (1) a (bottom) aqueous phase, (2) a (top) phase comprising an oil-in-water emulsion, (3) at least one anionic surfactant chosen from the sodium salts of esters of dimethicone copolyol and sulphosuccinic acid.

The sodium salts of esters of dimethicone copolyol and sulphosuccinic acid are known surfactants which are already used in cosmetic compositions, but their use has never been described for obtaining compositions which exist in the form of two separate phases which are, for example, one above the other in the same container, which phases are shaken at the time of use and which separate again at rest. Thus, document US-A-2002/0010110 describes an extrudable composition comprising two phases which are next to each other, separated by a separating layer, and which are extruded together from the container containing them by a common outlet, one of the phases being an isotropic phase and the other being a lamellar phase. Among the surfactants described are dimethicone copolyol sulphosuccinate. However, the compositions disclosed in this document do not necessarily contain dimethicone copolyol sulphosuccinate as surfactant, whereas, in the present application, the sodium salts of dimethicone copolyol and of sulphosuccinic acid make it possible to achieve the aim of the invention. In addition, in this document, one of the phases is a lamellar phase and the compositions described contain overall a large quantity of surfactants, whereas, in the presence invention, the top phase of the two-phase composition, which is in the form of an emulsion, does not constitute a lamellar phase, and the total surfactant content is at most 20% by weight relative to the total weight of the two-phase composition. Moreover, in the compositions disclosed in that document, the two phases are not one above the other, and when they are mixed and then allowed to stand, they do not undergo phase separation into two separate phases. That document therefore describes a composition different from the one claimed.

Since the composition according to the invention is preferably intended for topical application, it contains a physiologically acceptable medium, i.e. a medium compatible with the skin, the mucous membranes, the hair and the scalp. The composition may be especially a cosmetic or dermatological composition.

The anionic surfactant used according to the invention has the advantage not only of being effective for a gentle makeup removal, but also of allowing the production of a two-phase composition containing a phase in the form of an emulsion, without the use of another emulsifier.

The composition according to the invention comprises at least one aqueous phase and one emulsion constituting a phase that is separate from the aqueous phase. These two phases are separate, i.e. they are visible one above the other when in contact at rest and they therefore visually appear as not being mixed when they are at rest. The aqueous phase constitutes the bottom phase while the emulsion constitutes the top phase. In addition, according to one characteristic of the invention, the emulsion is not transparent, but has the appearance of a milk. The aqueous phase is generally preferably transparent. The two phases may be coloured or colourless.

The emulsion constituting the top phase should be considered as forming a single phase in the two-phase composition of the invention, although it is known that emulsions have at least two immiscible phases dispersed in each other. It can be considered as forming a single phase of the claimed composition because it is an emulsion which remains stable over time, i.e. several months and even several years without phase separation or decantation occurring, and this emulsion constitutes one phase of the two-phase composition according to the invention while the aqueous phase constitutes the other phase, the emulsion and the aqueous phase being arranged one above the other. During use, they are shaken in order to give a homogeneous emulsion which remains in the form of a homogeneous emulsion for only a short period, generally a few minutes or at the very most a few hours, and which separates again at rest into an aqueous phase and an emulsion phase.

The weight ratio between the aqueous phase and the emulsion is not particularly limited and may range, for example, from 25/75 to 90/10, preferably 30/70 to 70/30, and better still from 40/60 to 60/40.

The amount of aqueous constituents comprising the bottom aqueous phase and the aqueous phase of the emulsion generally similarly is not limited and generally represents from 10 to 90% by weight, preferably from 20 to 85% by weight, better still from 30 to 80% by weight and even better still from 40 to 70% by weight relative to the total weight of the composition. Moreover, the bottom aqueous phase and the aqueous phase of the emulsion may have the same composition.

Anionic Surfactant

The composition according to the invention contains at least one anionic surfactant chosen from the sodium salts of esters of dimethicone copolyol and sulphosuccinic acid.

They are especially compounds of formula (I):

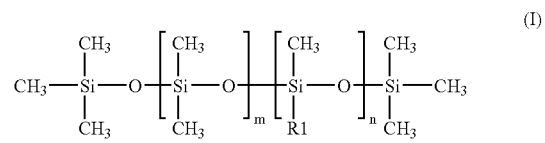

in which $R_1$ may represent, independently:

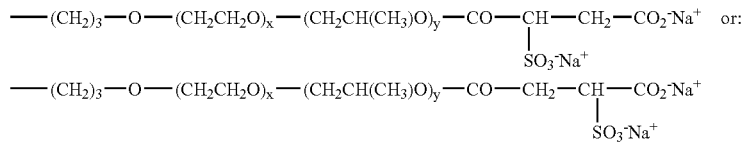

where m, n, x and y are integers which vary according to the dimethicone copolyol used: m and n independently may range, for example, from 2 to 100, and better still from 2 to 50; x may range, for example, from 1 to 50, and better still from 2 to 40, y may range, for example, from 0 to 50. Since n is greater than 1 both of the above $R_1$ groups may be present in the formula (I) anionic surfactant.

According to a preferred embodiment of the invention, the dimethicone copolyol used comprises only oxyethylenated groups, i.e. in the formula for R1, y=0.

Preferably, the surfactant chosen from the sodium salts of esters of dimethicone copolyol and of sulphosuccinic acid is Disodium PEG-12 Dimethicone sulphosuccinate (CTFA name), a compound of formula (I) where m=8, n=3, y=0 and x=12. As disodium PEG-12 dimethicone sulphosuccinate, mention may be made in particular of those sold by the company McIntyre either at 50% in aqueous solution under the name Mackanate DC 50, or at 30% in aqueous solution under the name Mackanate DC 30.

The amount of surfactant chosen from the sodium salts of esters of dimethicone copolyol and sulphosuccinic acid, as amount of active material, is variable, especially according to the overall relative proportions of oily constituents and of aqueous constituents and according to the final use of the composition. Indeed, if the composition constitutes a care product for the skin, it will likely contain less anionic surfactant dimethicone sulphosuccinate than if it constitutes a makeup-removing product where this surfactant will also play a makeup-removing role.

This amount of anionic surfactant, as active material, may range, for example, from 0.1 to 20% by weight, preferably from 0.2 to 15% by weight, better still from 0.2 to 10% by weight relative to the total weight of the composition. More specifically, the amount of anionic surfactant, as active material, in the makeup-removing product, may range, for example, from 0.5 to 20%, preferably from 1 to 15% and better still from 1 to 10% by weight relative to the total weight of the composition, and the amount of active material in a care product may range, for example, from 0.2 to 20%, preferably from 0.5 to 15% and better still from 1 to 10% by weight relative to the total weight of the composition.

Preferably, the total amount of surfactants is at most 15% by weight relative to the total weight of the composition.

The anionic surfactant used according to the invention is generally introduced into the aqueous phase.

According to a preferred embodiment of the invention, the composition contains, as sole surfactant, the sodium salts of esters of dimethicone copolyol and of sulphosuccinic acid. It is in particular preferably free of fatty acid, of fatty alcohol, of fatty acid ester of polyol, and of trihydroxystearin.

Aqueous Phase

The aqueous phase of the composition according to the invention constitutes the bottom phase. Moreover, the emulsion which constitutes the top phase of the two-phase composition is an oil-in-water emulsion (oily phase dispersed in the aqueous phase) and therefore contains an external aqueous phase which contains water and optionally certain water-soluble compounds, although these may be partially or totally present in the bottom aqueous phase. The aqueous phase of the emulsion and the bottom aqueous phase of the two-phase composition constitute the overall amount of aqueous phase and may the same composition.

For example, during the manufacture of the two-phase composition, the aqueous constituents and the oily constituents can be mixed and part of the aqueous phase can become the external phase of the emulsion while the other part can constitute the bottom aqueous phase. The term "aqueous phase" therefore means below both the bottom aqueous phase of the two-phase composition and the aqueous phase of the O/W emulsion.

As indicated above, the overall amount of aqueous constituents in the composition according to the invention may range, for example, from 10 to 90% by weight, preferably from 20 to 80% by weight, better still from 30 to 70% by weight and even better still from 40 to 60% by weight relative to the total weight of the composition.

The aqueous phase comprises water and, if desired, one or more of any water-soluble or water-dispersible additive. The water used may be any water, including tap, sterile demineralized water and/or a floral water such as rosewater, cornflower water, camomile water or lime water, and/or a natural mineral water or spring water, for instance: eau de Vittel, waters from the Vichy basin, eau d'Uriage, eau de la Roche Posay, eau de la Bourboule, eau d'Enghien-les-Bains, eau de Saint Gervais-les-Bains, eau de Neris-les-Bains, eau d'Allevar-les-Bains, eau de Digne, eau de Maizieres, eau de Neyrac-les-Bains, eau de Lons-le-Saunier, les Eaux Bonnes, eau de Rochefort, eau de Saint Christau, eau des Fumades, eau de Tercis-les-bains and eau d'Avene. The aqueous phase may also comprise reconstituted spring water, i.e. water containing trace elements such as zinc, copper, magnesium, etc., which reconstitutes the characteristics of a spring water.

Water-soluble additives that may especially be mentioned include polyols such as glycerol and glycols such as butylene glycol, hexylene glycol, polyethylene glycols and polypropylene glycol. The polyols may be present in an amount ranging from 0 to 25% by weight, preferably from 3 to 20%, better still from 3 to 15% by weight and even better still from 5 to 10% by weight relative to the total weight of the composition. According to one preferred embodiment of the invention, the composition contains at least one polyol, preferably glycerol or butylene glycol, or mixtures thereof.

Water-soluble additives that may also be mentioned include $C_2$-$C_8$ primary alcohols, and especially ethanol. According to one particular embodiment of the invention, the composition is preferably virtually free of ethanol. The expression "virtually free of ethanol" means herein a composition containing less than 5% by weight and preferably less than 2% by weight of ethanol relative to the total weight of the composition.

Emulsion

The oil-in-water (O/W) emulsion constitutes the top phase of the emulsion, and it comprises an external aqueous phase and an oily phase containing the oils and other fatty substances or lipophilic additives, dispersed in the aqueous phase. The emulsion generally represents from 10 to 75%, preferably from 30 to 70% by weight, and better still from 40 to 60% by weight relative to the total weight of the composition.

The O/W emulsion of the composition according to the invention comprises an oily phase dispersed in an aqueous phase.

The composition according to the invention may contain one or more oils in the oily phase of the emulsion constituting the top phase of the two-phase composition. These oils may be mineral, vegetable or synthetic oils, or silicone oils. Liposoluble or lipodispersible additives may also be present in the oily phase.

According to one preferred embodiment of the invention, the composition comprises one or more oils chosen from hydrocarbon-based oils of mineral or synthetic origin and silicone oils. More particularly, the composition advantageously contains one or more volatile oils chosen from volatile hydrocarbon-based oils of mineral or synthetic origin and volatile silicone oils.

The term "hydrocarbon-based oil" means an oil formed essentially from, or even consisting of, carbon and hydrogen atoms, and possibly oxygen and nitrogen atoms, and containing no silicon or fluorine atoms; it may contain ester, ether, amine or amide groups.

Volatile hydrocarbon-based oils of mineral or synthetic origin that may be mentioned include $C_8$-$C_{16}$ isoalkanes (also known as isoparaffins), such as isododecane, isodecane and isohexadecane, for instance the isoalkanes sold under the trade name Isopar by the company Exxon Chemical or the oils sold under the trade name Permethyl by the company Presperse; and mixtures thereof.

Non-volatile hydrocarbon-based oils of mineral or synthetic origin that may be mentioned include liquid petroleum jelly and hydrogenated polyisobutene such as Parleam® oil; and mixtures thereof.

The term "silicone oil" means an oil containing at least one silicon atom, and especially containing Si—O groups. The silicone oil may be chosen from non-volatile silicone oils and volatile silicone oils, and mixtures thereof.

The volatile silicone oils that may be used in the invention may be chosen from silicone oils with a flashpoint ranging from 40° C. to 102° C., preferably with a flashpoint of greater than 55° C. and less than or equal to 95° C., and preferentially ranging from 65° C. to 95° C. Volatile silicone oils that may be mentioned include linear or cyclic silicone oils containing from 2 to 7 silicon atoms, these silicones optionally comprising alkyl or alkoxy groups containing from 1 to 10 carbon atoms. Examples of volatile silicone oils that may especially be mentioned include cyclopoly-dimethylsiloxanes (INCI name: cyclomethicone), such as cyclopentasiloxane, cyclohexasiloxane, octamethylcyclo-tetrasiloxane, decamethylcyclopentasiloxane and dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane and dodecamethylpentasiloxane; and mixtures thereof.

The non-volatile silicone oil that may be used in the invention may be chosen from polydimethyl-siloxanes (PDMSS) and phenylated polymethylsiloxanes such as phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethyl-phenylsiloxanes; polysiloxanes modified with fatty acids, fatty alcohols or polyoxyalkylenes, and mixtures thereof.

Preferably, the composition according to the invention contains at least one volatile oil chosen from isoalkanes, volatile silicone oils, and mixtures thereof. According to another preferred embodiment of the invention, the oily phase contains at least one isoalkane chosen from isododecane and isohexadecane, and at least one volatile silicone oil.

Moreover, the oily phase may contain one or more other volatile or non-volatile oils, chosen from hydrocarbon-based oils of animal or plant origin, synthetic esters and ethers, fatty alcohols and fluoro oils, and mixtures thereof.

The term "fluoro oil" means an oil containing at least one fluorine atom.

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot kernel oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;

synthetic esters and ethers, especially of fatty acids, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance Purcellin oil, isononyl isononanoate, isopropyl myristate, isopropyl palmitate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate.

The oils may optionally be all solely volatile oils.

The amount of oily phase of the emulsion of the composition according to the invention is not particularly limited and may vary widely according to the purpose of the composition. It may range, for example, from 5 to 50% by weight, preferably from 10 to 40% by weight and better still from 15 to 35% by weight relative to the total weight of the composition.

Additives

The composition according to the invention may contain cosmetic adjuvants or additives, which will be in one or the other phase depending on their hydrophilic or lipophilic nature, for instance fragrances, preserving agents and bactericides, dyes, softeners, buffers, humectants, UV-screening agents (or sunscreens), electrolytes such as sodium chloride as indicated above, or a pH regulator (for example citric acid or sodium hydroxide), agents which facilitate phase separation, polymers, and mixtures thereof.

Preserving agents that may be used include any preserving agent usually used in the fields under consideration, for instance parabens, chlorhexidine gluconate and polyhexamethylene biguanide hydrochloride (CTFA name: polyaminopropyl biguanide). According to one preferred embodiment of the invention, the composition contains polyhexamethylene biguanide hydrochloride, alone or as a mixture with other preserving agents.

Examples of bactericides that may be used include a glyceryl mono($C_3$-$C_9$)alkyl or mono($C_3$-$C_9$)alkenyl ether, the manufacture of which is described in the literature, in particular in E. Baer, H.O.L. Fischer—J. Biol. Chem. 140-397-1941. Among these glyceryl mono($C_3$-$C_9$)alkyl or mono($C_3$-$C_9$)alkenyl ethers, 3-[(2-ethylhexyl)oxy]-1,2-propanediol, 3-[(heptyl)oxy]-1,2-propanediol, 3-[(octyl)oxy]-1,2-propanediol and 3-[(allyl)oxy]-1,2-propanediol are preferably used. A glyceryl mono($C_3$-$C_9$)alkyl ether that is more particularly preferred according to the present invention is 3-[(2-ethylhexyl)oxy]-1,2-propanediol, sold by the company Schulke & Mayr GmbH under the trade name Sensiva SC 50 (INCI name: ethylhexylglycerin).

Among the softeners that may be mentioned in particular are allantoin, bisabolol, planktons, and certain plant extracts, for instance extracts of rose and extracts of melilot.

The active agent(s) that may be present depend(s) on the final purpose of the composition. As active agents that may be used in the composition of the invention, especially when it concerns a skin care composition, examples that may be mentioned include enzymes (for example lactoperoxidase, lipase, protease, phospholipase and cellulases); flavonoids, such as isoflavones; moisturizers such as protein hydrolysates; sodium hyaluronate; anti-inflammatory agents; procyannidol oligomers; vitamins, for instance vitamin A (retinol), vitamin E (tocopherol), vitamin C (ascorbic acid), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; retinoids such as carotenoids and vitamin A derivatives; hydrocortisone; melatonin; algal extracts, fungal extracts, plant extracts, yeast extracts or bacterial extracts; steroids; antibacterial active agents, for instance 2,4,4'-trichloro-2'-hydroxydiphenyl ether (or triclosan), 3,4,4'-trichlorocarbanilide (or triclocarban) and the acids indicated above, and especially salicylic acid and its derivatives; tensioning agents; ceramides; essential oils; and mixtures thereof; and any active agent that is suitable for the final purpose of the composition.

UV-screening agents may be present in the composition according to the invention, especially when it is intended for antisun care. These screening agents may especially be organic screening agents, and may be present in an active-material amount ranging from 0.01 to 20% by weight of active material, preferably from 0.1 to 15% by weight and better still 0.2 to 10% by weight relative to the total weight of the composition.

As examples of UV-A-active and/or UV-B-active organic screening agents that may be added to the composition of the invention, examples that may be mentioned include derivatives containing a sulphonic function, such as sulphone-containing or sulphonate-containing derivatives of benzylidenecamphor, of benzophenone or of phenylbenzimidazole, more particularly benzylidenecamphor derivatives, for instance benzene-1,4-bis(3-methylidenecamphor-10-sulphonic acid) (INCI name: Terephthalylidenedicamphorsulphonic acid) manufactured under the name "Mexoryl SX" by the company Chimex, 3-benzylidenecamphor-4'-sulphonic acid (INCI name: Benzylidenecamphorsulphonic acid), manufactured under the name "Mexoryl SL" by the company Chimex, 2-[4-(camphormethylidene)phenyl]-benzimidazole-5-sulphonic acid and phenylbenzimidazole-sulphonic acid (INCI name: Phenylbenzimidazolesulphonic acid), sold under the name Eusolex 232 by the company Merck; para-aminobenzoic acid derivatives; salicylic derivatives such as ethylhexyl salicylate sold under the trade name Neo Heliopan OS by Haarmann and Reimer; dibenzoylmethane derivatives such as butylmethoxydibenzoylmethane sold especially under the trade name Parsol 1789 by Hoffmann La Roche; cinnamic derivatives such as ethylhexyl methoxycinnamate sold especially under the trade name Parsol MCX by Hoffmann La Roche; β,β'-diphenylacrylate derivatives such as octocrylene (2-ethylhexyl α-cyano-β,β-diphenylacrylate) sold under the trade name Uvinul N539 by the company BASF; benzophenone derivatives such as Benzophenone-1 sold under the trade name Uvinul 400 by BASF, Benzophenone-2 sold under the trade name Uvinul D50 by BASF, Benzophenone-3 or Oxybenzone, sold under the trade name Uvinul M40 by BASF, Benzophenone-4 sold under the trade name Uvinul MS40 by BASF; benzylidene-camphor derivatives such as 4-methylbenzylidenecamphor sold under the trade name Eusolex 6300 by Merck; phenylbenzimidazole derivatives such as Benzimidazilate sold under the trade name Neo Heliopan AP by Haarmann and Reimer; triazine derivatives such as Anisotriazine sold under the trade name Tinosorb S by Ciba Geigy and ethylhexyltriazone sold especially under the trade name Uvinul T150 by BASF; phenylbenzotriazole derivatives such as Drometrizole Trisiloxane sold under the trade name Silatrizole by Rhodia Chimie; anthranilic derivatives such as menthyl anthranilate sold under the trade name Neo Heliopan MA by Haarmann and Reimer; imidazoline derivatives; benzalmalonate derivatives; and mixtures thereof.

The compositions according to the invention may be prepared by any appropriate process. According to a preferred embodiment, the compositions of the invention are prepared by mixing, on the one hand, the aqueous or hydrophilic constituents and, on the other hand, the oily or lipophilic constituents forming the oily phase of the emulsion, by optionally heating between 40 and 50° C., by pouring the mixture of oily constituents into the mixture of aqueous constituents and shaking for about 10 to 30 minutes, and then allowing to stand until phase separation into an aqueous bottom phase and a nontransparent top phase of an emulsion occurs.

The compositions described above may be packaged in a single-compartment bottle. The user may then shake the bottle before use—e.g., applying some of the contents thereof to a pad of cotton wool. Provision may also be made for the two phases of the composition to be introduced into two independent compartments of the same bottle, a system being provided to mix them together at the time of distribution. Such devices are described, for example, in documents EP-A-497 256 and FR-A-2 697 233.

The composition according to the invention may be used for any topical application; especially, it may constitute a cosmetic or dermatological composition.

It may be used in particular for caring for, cleansing and/or removing makeup from the skin, the lips and/or the eyes, and also as a hair care composition.

A subject of the invention is also the cosmetic use of a cosmetic composition as defined above, for caring for, removing makeup from and/or cleansing the skin, the lips and/or the eyes, and/or for hair care.

A subject of the present invention is also a cosmetic process for removing makeup from, cleansing and/or caring for the skin, the lips and/or the eyes, wherein a cosmetic composition as defined above is applied to the skin, the lips and/or the eyes.

A subject of the present invention is also a cosmetic hair care process, wherein a cosmetic composition as defined above is applied to the hair.

The examples below of compositions according to the invention are given for illustrative purposes and with no limiting nature. The amounts therein are given as percentages by weight, unless otherwise mentioned.

EXAMPLE 1

| Skin care composition | |
|---|---|
| Oily phase: | |
| Cyclopentasiloxane | 7% |
| Isohexadecane | 2% |
| Hydrogenated polyisobutene | 8% |
| Lipophilic preservative | 0.4% |
| Vitamin E | 0.7% |
| Fragrance | 0.3% |
| Aqueous constituents | |
| Glycerin | 7% |
| Butylene glycol | 4% |
| Sodium hyaluronate (moisturizer) | 0.5% |
| Hydrophilic preservative | 0.2% |
| Mackanate DC 50 containing 50% active material (that is 2.5% of disodium PEG-12 dimethicone sulphosuccinate) | 5% |
| Demineralized water | qs 100% |

Procedure: The mixture of the aqueous constituents was prepared, on the one hand, and the constituents of the oily phase were mixed, on the other hand. The oily phase was then poured into the mixture of aqueous constituents and shaken.

A composition was obtained, which, at rest, comprises an aqueous phase and an emulsion which are separate. When they are shaken, a single emulsion is formed. After stopping the shaking, the two phases rapidly separate, that is to say after a period which may be from one minute to 30 minutes.

The two-phase composition obtained had good moisturizing properties and may be used in particular for moisturizing the skin.

EXAMPLE 2

| Makeup-removing composition | |
|---|---|
| Oily phase: | |
| Cyclopentasiloxane | 7% |
| Isohexadecane | 20% |
| Hydrogenated polyisobutene | 10% |
| Lipophilic preservative | 0.2% |
| Fragrance | 0.3% |
| Aqueous constituents | |
| Glycerin | 4% |
| Butylene glycol | 6% |
| Hydrophilic preservative | 0.3% |
| Mackanate DC 50 containing 50% active material (that is 10% of disodium PEG-12 dimethicone sulphosuccinate) | 20% |
| Demineralized water | qs 100% |

Procedure: The mixture of the aqueous constituents was prepared, on the one hand, and the constituents of the oily phase were mixed, on the other hand. These mixtures were heated to 40-50° C. and then the oil constituents were poured into the aqueous mixture and shaken.

A composition was obtained, which, at rest, comprises an aqueous phase and an emulsion which are separate. When they are shaken, a single emulsion is formed. After stopping the shaking, the two phases rapidly separate, that is to say after a period which may be from one minute to 30 minutes.

Analysis of the two separated phases shows that the top part was composed of the emulsion (emulsion in milk form) comprising 37.5% of oily phase, 20% of surfactant and between 5 and 10% of aqueous phase, and that the bottom phase was an aqueous phase comprising 4% of glycerin, 6% of butylene glycol, 0.3% of preservative, the remainder being water.

The two-phase composition obtained had good makeup-removing properties and may be used in particular for removing makeup from the skin and the eyes.

EXAMPLE 3

| Makeup-removing composition | |
|---|---|
| Oily phase: | |
| Cyclopentasiloxane | 4% |
| Isoparaffin | 3% |
| Isohexadecane | 25% |
| Hydrogenated polyisobutene | 7% |
| Lipophilic preservative | 0.2% |
| Vitamin E | 0.7% |
| Fragrance | 0.3% |
| Aqueous constituents | |
| Glycerin | 5% |
| Butylene glycol | 6% |
| Propylene glycol | 2% |
| Hydrophilic preservative | 0.3% |
| Mackanate DC 50 containing 50% active material (that is 15% of disodium PEG-12 dimethicone sulphosuccinate) | 30% |
| Demineralized water | qs 100% |

Procedure: The mixture of the aqueous constituents was prepared, on the one hand, and the constituents of the oily phase were mixed, on the other hand. These mixtures were heated to around 40-50° C. and then the oil constituents were poured into the aqueous mixture and shaken.

A composition was obtained, which, at rest, comprises an aqueous phase and an emulsion which are separate. When they are shaken, a single emulsion is formed. After stopping the shaking, the two phases rapidly separate, that is to say after a period which may be from one minute to 30 minutes.

The two-phase composition obtained had good makeup-removing properties and may be used in particular for removing makeup from the skin and the eyes.

The above written description of the invention provides a manner and process of making and using it such that any person skilled in this art is enabled to make and use the same, this enablement being provided in particular for the subject matter of the appended claims, which make up a part of the original description, and including preferred embodiments such as a composition for topical application, consisting of two separate phases, one above the other, comprising (1) a bottom aqueous phase, (2) a top phase consisting of an oil-in-water emulsion, (3) at least one anionic surfactant chosen from the sodium salts of esters of dimethicone copolyol and of sulphosuccinic acid.

As used above, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition comprising two separate phases, one above the other, said composition comprising:
   (1) a bottom aqueous phase,
   (2) a top phase comprising an oil-in-water emulsion, and
   (3) at least one anionic surfactant chosen from the sodium salts of esters of dimethicone copolyol and sulphosuccinic acid, wherein the total amount of surfactants is at most 15% by weight relative to the total weight of the composition.

2. The composition according to claim 1, wherein the weight ratio between the aqueous phase and the emulsion is 25/75 to 90/10.

3. The composition according to claim 1, wherein the oil-in-water emulsion comprises an aqueous phase and wherein the bottom aqueous phase and the aqueous phase of the oil-in-water emulsion have the same constitution.

4. The composition according to claim 1, comprising at least one surfactant of formula (I):

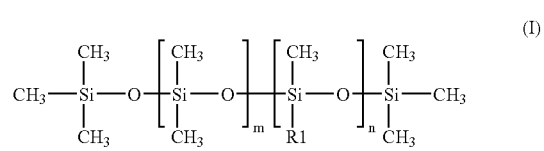

in which $R_1$ is, independently:

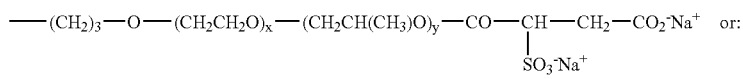

-continued

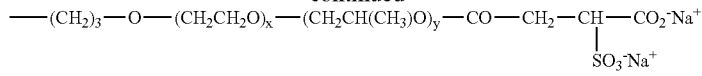

or:
where m and n independently range from 2 to 100; x ranges from 1 to 50, y ranges from 0 to 50.

5. The composition according to claim 1, comprising disodium PEG-12 dimethicone suiphosuccinate.

6. The composition according to claim 1, wherein the amount of surfactant chosen from the sodium salts of esters of dimethicone copolyol and suiphosuccinic acid is 0.1 to 15% by weight relative to the total weight of the composition.

7. The composition according to claim 1, wherein it comprises one or more oils chosen from hydrocarbon-based oils of mineral or synthetic origin, silicone oils, and mixtures thereof.

8. The composition according to claim 1, wherein it comprises at least one volatile oil chosen from isoalkanes, volatile silicone oils, and mixtures thereof.

9. The composition according to claim 1, wherein it comprises a total amount of aqueous constituents ranging from 10 to 90% by weight relative to the total weight of the composition.

10. The composition according to claim 1, wherein said composition is a cosmetic or dermatological composition.

11. The composition according to claim 2, wherein the weight ratio between the aqueous phase and the emulsion is 30/70 to 60/40.

12. The composition according to claim 6, wherein the amount of surfactant chosen from the sodium salts of esters of dimethicone copolyol and suiphosuccinic acid is 0.2 to 15% by weight relative to the total weight of the composition.

13. The composition according to claim 9, wherein it comprises a total amount of aqueous constituents ranging from 20 to 80% by weight relative to the total weight of the composition.

14. A process for caring for, removing makeup from and/or cleansing the skin, the lips and/or the eyes, and/or for hair care, comprising applying the composition of claim 1 to the skin, the lips, the eyes, and/or the hair.

15. A process for removing makeup from, cleansing and/or caring for the skin, the lips and/or the eyes, comprising applying the composition of claim 1 to the skin, the lips and/or the eyes.

16. A process for caring for hair, wherein a composition according to claim 1 is applied to the hair.

* * * * *